United States Patent [19]
Lavielle et al.

[11] Patent Number: 6,162,822
[45] Date of Patent: Dec. 19, 2000

[54] BISIMIDE COMPOUNDS

[75] Inventors: Gilbert Lavielle, La Celle Saint Cloud; Patrick Hautefaye, Servon Brie Comte Robert; Ghanem Atassi, Saint Cloud; Alain Pierre, Marly Le Roi; Laurence Kraus-Berthier, Colombes; Stéphane Leonce, Versailles, all of France

[73] Assignee: Adir et Compagnie, Courbevoie, France

[21] Appl. No.: 09/221,904

[22] Filed: Dec. 28, 1998

Related U.S. Application Data

[62] Division of application No. 08/899,289, Jul. 23, 1997, Pat. No. 5,854,273.

Foreign Application Priority Data

Jul. 26, 1996 [FR] France .................................. 96.09417

[51] Int. Cl.[7] .......................... A01N 43/38; A61R 31/40; C07D 487/00; C07D 491/00; C07D 487/02
[52] U.S. Cl. ..................... 514/410; 514/410; 514/411; 548/421; 548/423; 548/429; 548/430; 548/431; 548/433
[58] Field of Search ...................... 548/421, 423, 548/429, 430, 431, 433; 514/410, 411

[56] References Cited

U.S. PATENT DOCUMENTS 3,873,567  3/1975  Cyba ........................................ 260/326
5,416,089  5/1995  Patten et al. ............................ 514/284

*Primary Examiner*—Mukund J. Shah
*Assistant Examiner*—Ben Schroeder
*Attorney, Agent, or Firm*—The Firm of Gordon W. Hueschen

[57] ABSTRACT

A compound of formula (I)

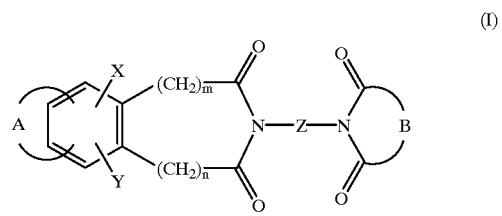

in which:

m, and n, which may be identical or different, represent 0 or 1,

X and Y, which may be identical or different, represent hydrogen or halogen or alky, trihaloalkyl, alkoxy, hydroxyl, cyano, nitro, amino, alkylamino or dialkylamino, Z represent a linear or branched $C_4$ to $C_{12}$ alkylene chain in which one or more —$CH_2$— are optionally replaced by any one of the following atoms or groups: —NR—, —O—, —S—, —SO—, —$SO_2$—, or —CONH—, or by a substituted or unsubstituted heterocylcic, A forms, with two adjacent carbon atoms of the phenyl ring, a phenyl, naphthyl or tetrahydronaphthyl ring or a heterocycle,

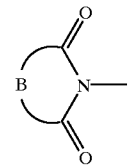

and medicinal products containing the same are useful as anticancer agent.

7 Claims, No Drawings

6,162,822

BISIMIDE COMPOUNDS

The present application is a division of our prior-filed application Ser. No. 08/899,289, filed Jul. 23, 1997, now U.S. Pat. No. 5,854,273.

BACKGROUND OF THE INVENTION

Compounds derived from bisimides have already been described in the literature. This is more particularly the case for the compounds described in patents EP 506 008, DE 4034687, WO 9500490 or DE 4232739.

DETAILED DESCRIPTION OF THE INVENTION

The compounds of the present invention have entirely original structures compared with those described in the prior art. They are either symmtrical or dissymmetrical compounds which have never been described previously. Moreover, the power of their pharmacological activities makes them particularly advantageous as new drugs that are useful in the treatment of cancers and in particular solid tumors.

More specifically, the present invention relates to the compounds of formula (I)

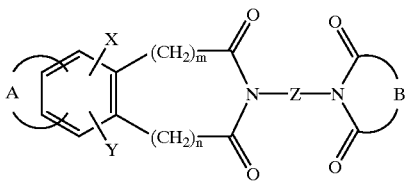

(I)

in which:

m, and n, which may be identical or different, represent 0 or 1,

X and Y, which may be identical or different, represent a hydrogen or halogen atom or a linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylamino or dialkylamino group, Z represent a linear or branched $C_4$ to $C_{12}$ alkylene chain in which one or more —$CH_2$— groups are optionally replaced by any one of the following atoms or groups: —NR— (in which R represents a hydrogen atom or a linear or branched ($C_1$–$C_6$) alkyl group), —O—, —S—, —SO—, —$SO_2$—, or —CONH—, or by a substituted or unsubstituted heterocyclic group, A forms, with two adjacent carbon atoms of the phenyl ring:

a substituted or unsubstituted phenyl ring,
a substituted or unsubstituted naphthyl ring,
a substituted or unsubstituted tetrahydronaphthyl ring or substituted or unsubstituted 1,4-dioxo-1,2,3,4-tetrahydronaphthyl ring, or a substituted or unsubstituted heterocycle,

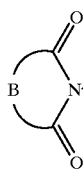 represents any one of the following groups:

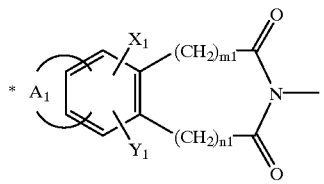

in which:

$m_1$ and $n_1$, which may be identical or different, represent 0 or 1, $X_1$ and $Y_1$, which may be identical or different, represent a hydrogen or halogen atom or a linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylamino or dialkylamino group, $A_1$ forms, with two adjacent carbon atoms of the phenyl ring:

a substituted or unsubstituted phenyl ring,
a substituted or unsubstituted naphthyl ring,
a substituted or unsubstituted tetrahydronaphthyl ring or substituted or unsubstituted 1,4-dioxo-1,2,3,4-tetrahydronaphthyl ring, or
a substituted or unsubstituted heterocycle,

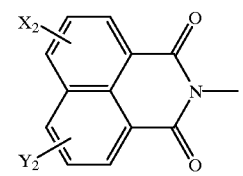

in which $X_2$, and $Y_2$, which may be identical or different, represent a hydrogen or halogen atom or a linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylamino or dialkylamino group, their isomers and their addition salts with a pharmaceutically acceptable acid or base.

Among the pharmaceutically acceptable acids which may be mentioned, without any limitation being implied, are hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, camphoric acid, etc.

Among the pharmaceutically acceptable bases which may be mentioned, without any limitation being implied, are sodium hydroxide, potassium hydroxide, triethylamine, tertbutylamine, etc.

The terms substituted or unsubstituted phenyl group, substituted or unsubstituted naphthyl group and substituted or unsubstituted tetrahydronaphthyl group are understood to refer to a phenyl, naphthyl or tetrahydronaphthyl group which is optionally substituted with one or more halogen atoms or linear or branched ($C_1$–$C_6$) alkyl, linear or branched ($C_1$–$C_6$) trihaloalkyl, linear or branched ($C_1$–$C_6$) alkoxy, hydroxyl, nitro or cyano groups or amino groups (optionally substituted with one or more linear or branched ($C_1$–$C_6$) alkyl groups).

The term substituted or unsubstituted heterocycle is understood to refer to a mono- or bicyclic, saturated or unsaturated 5- to 16-membered group containing 1, 2 or 3 hetero atoms chosen from oxygen, nitrogen and sulfur, it being understood that the heterocycle may optionally be substituted with one or more halogen atoms or linear or branched ($C_1$–$C_6$) alkyl, linear or branched ($C_1$–$C_6$) alkoxy, hydroxyl, trihalomethyl, nitro or cyano groups or amino groups (optionally substituted with one or more linear or branched ($C_1$–$C_6$) alkyl groups).

The preferred compounds according to the invention are those in which:

A forms, with two adjacent carbon atoms of the phenyl ring:
  a substituted or unsubstituted naphthyl ring,
  or a substituted or unsubstituted heterocycle preferably chosen from substituted or unsubstituted indole, substituted or unsubstituted benzo[b]thiophene and substituted or unsubstituted benzo[b]furan rings.

The preferred constitutents are those for which Z represents a $C_4$ to $C_{12}$ alkylene chain in which 1, 2 or 3 —$CH_2$— groups are replaced by 1, 2 or 3 —NR— groups (in which R represents a linear or branched ($C_1$–$C_6$) alkyl group).

The invention also covers the process for the preparation of the compounds of formula (I), which process uses, as starting material, an anhydride of formula (II):

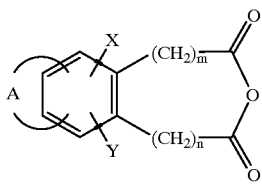
(II)

in which A, X, Y, m and n are as defined in formula (I), which is reacted with an excess of a diamine of formula (III):

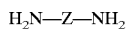
(III)

in which Z is as defined in formula (I),
in order to lead, after separation:
either to the compound of formula (I/a), a specific case of the compounds of formula (I):

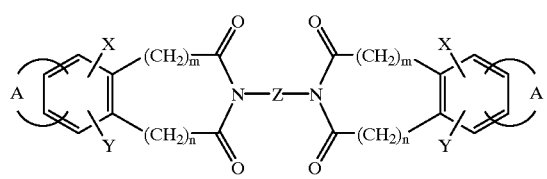
(I/a)

in which A, X, Y, Z, m and n have the same meaning as in formula (I), or to the compound of formula (IV):

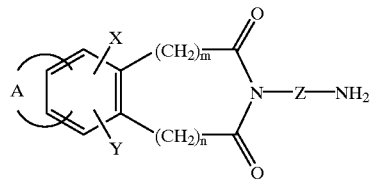
(IV)

in which A, X, Y, Z, m and n have the same meaning as in formula (I),
which is reacted:
  * either with the anhydride of formula (II/a):

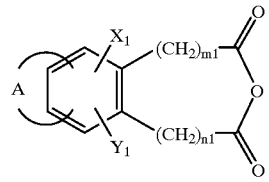
(II/a)

in which $A_1$, $X_1$, $Y_1$, $m_1$ and $n_1$ are as defined in formula (I), in order to lead to the compound of formula (I/b), a specific case of the compounds of formula (I):

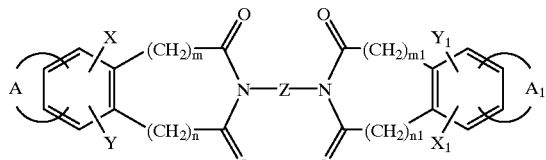
(I/b)

in which A, X, Y, m, n, Z, $A_1$, $X_1$, $Y_1$, $m_1$, and $n_1$ have the same meaning as in formula (I),
  * or with the anhydride of formula (V)

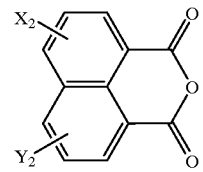
(V)

in which $X_2$ and $Y_2$ are as defined in formule (I),
in order to lead to the compound of formula (I/c), a specific case of the compounds of formula (I):

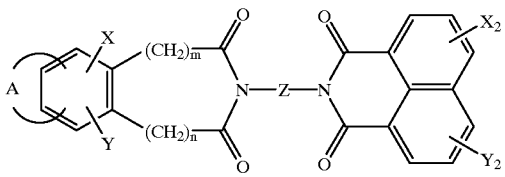
(I/c)

in which A, X, Y, $X_2$, $Y_2$, Z, m and n have the same meaning as in formula (I), which compound of formula (I/a), (I/b) or (I/c), may undergo, if so desired, standard reactions for the transformation of substituents on aromatic rings, which is purified, where appropriate, according to a standard purification technique, the isomers of which are optionally separated according to a standard separation technique and which is converted, if so desired, into its additon salts with a pharmaceutically acceptable acid or base.

The anhydrides of formula (II) or (V) are either commercial compounds or are obtained according to known procedures.

The invention also covers pharmaceutical compositions containing, as active principle, at least one compound of formula (I) with one or more inert, non-toxic, suitable excipients. Among the pharmaceutical compositions according to the invention which may be mentioned more particularly are those which are suitable for oral, parenteral (intravenous or subcutaneous) or nasal administration, simple or sugar-coated tablets, sublingual tablets, gelatin capsules, lozenges, suppositories, creams, ointments, dermal gels, injectable preparations, drinkable suspensions, etc.

The appropriate dosage may be adapted according to the nature and severity of the complaint, the route of administration and the age and weight of the patient. This dosage ranges from 0.1 to 400 mg per day in one or more dosage intakes.

The examples which follow illustrate the invention without, however, limiting it in any way.

The starting materials used are known products or are prepared according to known procedures.

The following preparations lead to synthetic intermediates that are useful for the preparation of compounds of the invention.

The structures of the compounds described in the examples and the preparations were determined according to the usual spectrophotometric techniques (infrared, NMR, mass spectrometry, etc.).

PREPARATION A

10-Methoxy-2-oxacyclopenta[c]phenanthrene-1,3-dione

Stage A: 2-Hydroxymethylene-7-methoxy-3,4-dihydro-2H-naphthalen-1-one

The expected product is prepared from 7-methoxy-1-tetralone and ethyl formate according to the procedure described in Organic Synthesis 1959, 39, 27.

Stage B: tert-Butyl 3-(7-methoxy-1-oxo-3,4-dihydro-1H-naphthalen-2-ylidene)-propionate 90 ml of a solution of 5 mmol of the product prepared in the above step and 6 mmol of tert-butyl triphenylphosphoranylideneacetate in methylene chloride is stirred for 2 hours at room temperature and under argon. The medium is concentrated under vacuum and the residue is crystallized from isopropyl ether. The precipitate is filtered off and the filtrate is concentrated to give 95% of a yellow product which crystallizes.

Melting point: 76° C.

Stage C: 9-Methoxy-5,6-dihydrobenzo[h]-chromen-2-one 6.5 ml of trifluoracetic anhydride and then 3.6 ml of trifluoracetic acid are added dropwise at room temperature to 10 ml of a solution of 4.6 mmol of the product prepared in the above stage in methylene chloride. The medium is then stirred for 4 hours, after which it is hydrolyzed with 30 ml of water. The aqueous phase is extracted with 30 ml of methylene chloride and the organic phase is washed with water, dried and concentrated under vacuum.

Melting point: 108–110° C.

Stage D : Dimethyl 6-methoxy-9, 10-dihydrophenanthrene-3,4-dicarboxylate

A solution of 5.3 mmol of the product prepared in the above stage and 2.6 ml of methyl acetylenedicarboxylate in 20 ml of dimethylformamide is maintained at reflux for 4 hours. The solvent is evaporated off under vacuum and the medium is poured into 40 ml of water and extracted with 3 times 10 ml of ether. The combined organic phases are washed with water and dried over magnesium sulfate. After evaporation of the solvent, the product is obtained, which crystallizes.

Melting point: 158–160° C.

Stage E: Dimethyl 6-methoxyphenanthrene-3,4-dicarboxylate.

The product prepared in the above stage is dissolved in 150 ml of dry toluene. 1.2 equivalents of dichlorodicyanoquinone are added and the medium is maintained at reflux for 4 hours. After cooling, the medium is filtered and the filtrate is evaporated. The residue is then taken up in 50 ml of water and the crude product is extracted with 3 times 10 ml of ether. After concentration of the solvent, the product is purified by chromatography on silica with $CH_2Cl_2$ eluent.

Melting point: 112–115° C.

Stage F: Methyl 4-methoxycarbonyl-6-methoxyphenanthrene-3-carboxylate and methyl 3-methoxycarbonyl-6-methoxyphenanthrene4-carboxylate A solution of the product prepared in the above step in 15 ml of 1 N sodium hydroxide and 20 ml of methanol is maintained at reflux for 3 hours. After cooling, the methanol is evaporated off and the aqueous phase is acidified with 6 N hydrochloric acid. The medium is extracted with 3 times 20 ml of methylene chloride and the products are obtained after evaportion of the solvent.

Stage G :10-Methoxy-2-oxacyclopenta[c]phenanthrene-1,3-dione

A mixture of the acids prepared in the above step in 120 ml of acetic anhydride is maintained at reflux for 24 h. After cooling, the precipitate is filtered off, washed with ether and dried.

Melting point: 238° C.

PREPARATION B

2-Oxacyclopenta[c]phenanthrene-1,3-dione

Stage A: Dimethyl phenanthrene-3,4-dicarboxylate

A solution of 65 mmol of 2-vinylnaphthalene and 68 mmol of methyl acetylene-dicarboxylate in 200 ml of nitrobenzene is maintained at reflux for 14 hours. After distillation of the solvent, the reaction medium is chromatographed on silica (eluent: $CH_2Cl_2$) in order to obtain the expected product.

Melting point: 117° C.

Stage B: 3-Methoxycarbonylphenanthrene-4-carboxylic acid and 4-methoxy-carbonylphenanthrene-3-carboxylic acid The mixture is prepared from the product described in stage A according to the process described in stage F of preparation A.

Melting point: 257° C.

Stage C: 2-Oxacyclopenta[c]phenanthrene- 1,3-dione

The expected product is prepared from the mixture described in the above stage according to the process described in stage G of preparation A.

Melting point: 245° C.

PREPARATION C

Naphtho[2,3-c]furan-1,3-dione

The expected product is obtained according to the process described in stage G of preparation A, starting with napthalene-2,3-dicarboxylic acid.

PREPARATION D
2-Oxa-8-thiadicyclopenta[a,h]naphthalene-1,3-dione

The expected product is obtained according to the process described in preparation A, using 6,7-dihydro-5H-benzo[b]thiophen4-one in stage A.

PREPARATION E
9-Aza-9,10-dimethyl-6-methoxy-2-oxa-9H-cyclopenta[b]fluorene-1,3-dione Stage A: Dimethyl 1,9-dimethyl-6-methoxy-9H-carbazole-2,3-dicarboxylate The expected product is prepared from 1,9-dimethyl-6-methoxy-9H-pyrano[3,4-b]indol-3-one according to the method described in *Chem. Ber,* 97, 667, 1964.

Stage B: 1,9-Dimethyl-6-methoxy-2-methoxycarbonyl-9H-carbazole-3-carboxylic acid and 1,9-dimethyl-6-methoxy-3-methoxycarbonyl-9H-carbazole-2-carboxylic acid.

The mixture is prepared from the product described in stage A according to the process described in stage F of preparation A.

Stage C: 9-Aza-9,10-dimethyl-6-methoxy-2-oxa-9H-cyclopenta[b]fluorene-1,3-dione

The expected product is obtained according to the process described in stage G of preparation A, starting with the compound described in the above stage.

PREPARATION F
10-Nitro-2-oxacyclopenta[c]phenanthrene-1,3-dione

Stage A: Dimethyl 6-nitrophenanthrene-3,4-dicarboxylate

A chilled solution of 38.8 mmol of 70% nitric acid is added dropwise to a suspension, cooled to 0° C., of 32.3 mmol of the product obtained in stage A of preparation B in 120 ml of trifluoroacetic anhydride. The medium is stirred for 3 h at 0° C. and then for 2 h at room temperature. The precipitate is then filtered off, washed with diisopropyl ether and dried.

Melting point: 180° C. with decomposition

Stage B: 6-Nitro-3-methoxycarbonylphenanthrene-4-carboxylic acid and 6-nitro-4-methoxycarbonylphenanthrene-3-carboxylic acid.

The mixture is prepared from the product obtained in the above step according to the process described in stage B of preparation G.

Stage C: 10-Nitro-2-oxacyclopenta[c]phenanthrene-1,3-dione

The product is obtained according to the process described in stage G of preparation A, starting with the mixture prepared in the above step.

PREPARATION G
9-Oxacyclopenta[b]phenanthrene-8,10-dione

Stage A: Ethyl naphthalen-1-ylacrylate 220 ml of a 1 N solution of potassium tert-butoxide in tetrahydrofuran are added dropwise to a solution of 0.219 mol of ethoxycarbonyltriphenylphosphonium bromide in 200 ml of tetrahydrofuran. The medium is stirred for 1 h at room temperature, after which a solution of 0.22 mol of naphthalene-1-carboxaldehyde in tetrahydrofuran is added dropwise. The medium is stirred for 4 h at room temperature, filtered, the solvent is evaporated off and the residue is taken up in 400 ml of methylene chloride. The organic phase is washed with 100 ml of water, dried and concentrated. The residue is taken up in diisopropyl ether, the precipitate is filtered off and the expected product is obtained after concentration of the solvent.

Stage B: Naphthalen-1-ylacrylic acid

A soluton of 0.2 mol of the compound prepared in the above step in 500 ml of ethanol is stirred for 18 h at room temperature in the presence of 250 ml of a 2 N solution of sodium hydroxide. The ethanol is concentrated, the medium is extracted with 100 ml of ethyl acetate and the aqueous phase is acidified at 0° C. with 6 N hydrochloric acid solution. The expected product is filtered off and dried.

Melting point: 188° C.

Stage C: 2,3-Dibromonaphthalen-1-ylpropionic acid

The expected product is prepared from the acid obtained in the above step according to the method described in *Aust. J. Chem.,* 16, 854, 1963.

Melting point: 197° C.

Stage D: Naphthalen-1-ylpropynoic acid

A mixture of 0.1 mol of the compound prepared in the above step in 120 ml of ethanol containing 0.36 mol of potassium hydroxide is stirred at reflux for 2 h and then at room temperature for 16 h. The precipitate is filtered off and the filtrate is concentrated. The residue is taken up in ether and the precipitate is filtered off, washed with dichloromethane and then diluted in 400 ml of water. The aqueous phase is acidified with concentrated hydrochloric acid and the expected product is filtered off, dried and recrystallized from carbon tetrachloride.

Melting point: 95° C.

Stage E: 9-Oxacyclopenta[b]phenanthrene-8,10-dione

The expected product is prepared from the compound prepared in the above step according to the method described in *Aust. J. Chem.,* 16, 854, 1963.

Melting point: 278° C.

PREPARATION H
Benzo[d]benzo[2,1-b;3-4-c']difuran-1,3-dione

Stage A: Methyl benzofuran-3-ylacetate

A mixture of 0.4 mol of coumaranone and 0.48 mol of methyl (triphenylphosphoranylidene)acetate in 1 liter of p-xylene is maintained at reflux for 18 h. After cooling to room temperature, the solvent is evaporated off, the residue is taken up in 1 liter of ether, the precipitate is filtered off and washed with ether, the filtrate is concentrated and the expected product is obtained after chromatography on silica (eluent: $CH_2Cl_2$).

Stage B: 2-Benzofuran-3-ylethanol

A solution of 0.38 mol of the product prepared in the above step is added to a suspension of 0.64 mol of $LiAlH_4$ in 1 liter of ether stirred at 0° C. The medium is stirred for 1 h at room temperature, followed by dropwise addition of 100 ml of ethyl acetate and then 100 ml of 1 N HCl. After stirring for 18 h, the medium is filtered, the filtrate is separated out by settling and the organic phase is washed with saturated NaCl solution and then with water. The expected product is obtained after drying the organic phase and evaporation of the solvent.

Stage C: 3-(2-Bromoethyl)benzofuran

The expected product is obtained from the compound prepared in the above step according to the procedure described in *Aust. J. Chem.,* 44, 907, 1991.

Stage D: 3-Vinylbenzofuran

The expected product is obtained from the compound prepared in the above step according to the procedure described in *Aust. J. Chem.,* 44, 907, 1991.

Stage E: Dimethyl 1,2-dihydrodibenzofuran-3,4-dicarboxylate

A solution of 0.2 mol of the compound prepared in the above step and 0.2 mol of methyl acetylenedicarboxylate in 1 liter of degassed toluene is maintained at reflux for 24 h under an inert atmosphere. After concentration of the solvent, the expected product is obtained by chromatography on silica (eluent: $CH_2Cl_2$).

Stage F: Dimethyl dibenzofuran-3,4-dicarboxylate

The expected product is obtained from the compound prepared in the above step according to the process described in stage G of preparation A.
Melting point: 123° C.

Stage G: Dibenzofuran-3,4-dicarboxylic acid

The expected product is obtained from the compound prepared in the above step according to the process described in stage B of preparation G.
Melting point: 260–262° C.

Stage H: Benzo[d]benzo[2,1-b;3-4-c']difuran-1,3-dione

The expected product is obtained from the compound prepared in the above step according to the process described in stage G of preparation A.
Melting point: 258° C.

PREPARATION I

Benzo[d]benzo[1,2-b; 3-4-c']difuran-1,3-dione

Stage A: 2-Vinylbenzofuran 92 ml of a 1 N solution of potassium tert-butoxide in tetrahydrofuran are added dropwise to a vigorously stirred mixture at 0° C. of 68.4 mmol of benzofuran-2-carboxaldehyde and 92 mmol of methyltriphenylphosphonium bromide in 200 ml of tetrahydrofuran and 150 ml of dimethylformamide. The medium is stirred for 2 h at room temperature, poured into 2 liters of ice-water and extracted with ether. After concentration of the solvents, the residue is taken up in 1 liter of petroleum ether and the precipitate is filtered off and washed with petroleum ether. The expected product is obtained by evaporation of the filtrate.

Stage B: Dimethyl dibenzofuran-1,2-dicarboxylate

The expected product is obtained from the compound prepared in the above step according to the process described in stage E of preparation H.
Melting point: 126° C.

Stage C: Dibenzofuran-1-methoxycarbonyl-2-carboxylic acid and dibenzofuran-2-methoxycarbonyl-1-carboxylic acid The expected product is obtained from the compound prepared in the above step according to the process described in stage B of preparation G.
Melting point: 175–176° C.

Stage D: Benzo[d]benzo[1,2-b; 3-4-c']difuran-1,3-dione

The expected product is obtained from the compound prepared in the above step according to the process described in stage G of preparation A.
Melting point: 211° C.

PREPARATION J

2-Oxa-6-thiacyclopenta[c]fluorene-1,3-dione

Stage A: Benzo[b]thiophene-2-carboxaldehyde

The expected product is obtained from benzo[b]thiophene according to the method decribed in *J.A.C.S.*, 74, 2396, 1952.
Melting point: 40–41° C.

Stage B: Vinyl-2-benzo[b]thiophene

The expected product is obtained from the compound prepared in the above step according to the process described in stage A of preparation I
Melting point: 132–134° C.

Stage C: Dimethyl 3,4-dihydrodibenzothiophene-1,2-dicarboxylate

The expected product is obtained from the compound prepared in the above step according to the process described in stage E of preparation H.
Melting point: 129° C.

Stage D: Dimethyl dibenzothiophene-1,2-dicarboxylate

The expected product is obtained from the compound prepared in the above step according to the process described in stage E of preparation A.

Stage E: 1-Methoxycarbonyldibenzothiophene-2-carboxylic acid and 2-methoxycarbonyldibenzothiophene-1-carboxalylic acid The expected product is obtained from the compound prepared in the above step according to the process described in stage B of preparation G.
Melting point: 248–250° C.

Stage F: 2-Oxa-6-thiacyclopenta[c]fluorene-1,3-dione

The expected product is obtained from the compound prepared in the above step according to the process described in stage G of preparation A.
Melting point: 269° C.

PREPARATION K

10-Methyl-10H-2-oxa-10-azacyclopenta[a]fluorene-1,3-dione

Stage A: 1-Methyl-3-vinyl-1H-indole

The expected product is obtained from 1-methyl-1H-indole-3-carboxaldehyde according to the process described in stage A of preparation I.

Stage B: Dimethyl 9-methyl4,9-dihydro-3H-carbazole-1,2-dicarboxylate

The expected product is obtained from the compound prepared in the above step according to the process described in stage E of preparation H.
Melting point :113° C.

Stage C: Dimethyl 9-methyl-3H-carbazole-1,2-dicarboxylate

The expected product is obtained from the compound prepared in the above step according to the process described in stage E of preparation A.
Melting point: 139° C.

Stage D: 9-Methyl-1-methoxycarbonyl-3H-indole-2-carboxylic acid and 9-methyl-2-methoxycarbonyl-3H-indole-1-carboxylic acid The expected product is obtained from the compound prepared in the above step according to the process described in stage B of preparation G.

Stage E: 10-Methyl-10H-2-oxa-10-azacyclopenta[a]fluorene-1,3-dione

The expected product is obtained from the compound prepared in the above step according to the process described in stage G of preparation A.
Melting point:>300° C.

PREPARATION L

6-Methyl-6H-2-oxa-6-azacyclopenta[c]fluorene-1,3-dione

Stage A: (1-Methyl-1H-indol-2-yl)methanol

The expected product is obtained from methyl 1-methyl-1H-indole-2-carboxylate according to the process described in stage B of preparation H.
Melting point: 104° C.

Stage B: 1-Methyl-1H-indole-2-carboxaldehyde

A mixture of 0.1 mol of the compound prepared in the above step, 1 mol of manganese oxide and 0.37 mol of sodium chloride in 500 ml of ether is stirred for 48 h at room temperature in a pressure vessel. The medium is filtered and concentrated and the expected product is obtained by chromatography on silica (eluent: $CH_2Cl_2$).
Melting point: 83° C.

Stage C: 1-Methyl-2-vinyl-1H-indole

The expected product is obtained from the compuond prepared in the above step according to the process described in stage A of preparation I.

Stage D: Dimethylester of 9-methyl-2,9-dihydro-9H-carbazole-3,4-dicarboxylic acid The expected product is obtained from the compound prepared in the above step according to the process described in stage E of preparation H.
Melting point: 153° C.

Stage E: Dimethylester of 9-methyl-9H-carbazole-3,4-dicarboxylic acid

The expected product is obtained from the compound prepared in the above step according to the process described in stage E of preparation A.
Melting point: 156° C.

Stage F: 9-Methyl-9H-carbazole-3,4-dicarboxylic acid

The expected product is obtained from the compound prepared in the above step according to the process described in stage B of preparation G.
Melting point :294° C.

Stage G: 6-Methyl-6H-2-oxa-6-azacyclopenta[c]fluorene-1,3-dione

The expected product is obtained from the compound prepared in the above step according to the process described in stage G of preparation A.
Melting point: >300° C.

PREPARATION M
6-Acetyl-6H-2-oxa-6-azacyclopenta[c]fluorene-1,3-dione
Stage A: (1H-Indol-2-yl)methanol The expected product is obtained from ethyl 1H-indole-2-carboxylate according to the process described in stage B of preparation H.
Melting point: 80° C.

Stage B: 1H-Indole-2-carboxaldehyde

The expected product is obtained from the compound prepared in the above step according to the process described in stage B of preparation L.

Stage C: 2-Vinyl-1H-indole

The expected product is obtained from the compound prepared in the above step according to the process described in stage A of preparation I.
Melting point :91° C.

Stage D: Dimethyl 2,9-dihydro-1H-carbazole-3,4-dicarboxylate

The expected product is obtained from the compound prepared in the above step according to the process described in stage E of preparation H.
Melting point: 249° C.

Stage E: Dimethyl 1H-carbazole-3,4-dicarboxylate

The expected product is obtained from the compound prepared in the above step according to the process described in stage E of preparation A.
Melting point :219° C.

Stage F: 3-Methoxycarbonyl-1H-carbazole4-carboxylic acid and 4-methoxycarbonyl-1H-carbazole-3-carboxylic acid The expected product is obtained from the compound prepared in the above step according to the process described in stage B of preparation G.

Stage G: 6-Acetyl-6H-2-oxa-6-azacyclopenta[c]fluorene-1,3-dione

The expected product is obtained from the compound prepared in the above step according to the process described in stage G of preparation A.

PREPARATION N
6-Methyl-9-nitro-6H-2-oxa-6-azacyclopenta[c]fluorene-1,3-dione
Stage A: Dimethyl 6-nitro-9-methyl-9H-carbazole-3,4-dicarboxylate The expected product is obtained from the compound prepared in stage E of preparation L according to the process described in stage A of preparation F.
Melting point: 234° C.

Stage B: 6-Nitro-9-methyl-9H-carbazole-3,4-dicarboxylic acid

The expected product is obtained from the compound prepared in the above step according to the process described in stage F of prepartion A.

Stage C: 6-Methyl-9-nitro-6H-2-oxa-6-azacyclopenta[c]fluorene-1,3-dione

The expected product is obtained from the compound prepared in the above step according to the process described in stage G of preparation A.
Melting point: >300° C.

PREPARATION O
6-Methyl-9-methoxy-6H-2-oxa-6-azacyclopenta[c]fluorene-1,3-dione
Stage A: Methyl 5-methoxy-1-methyl-1H-indolecarboxylate 100 ml of a 1 N solution of potassium tert-butoxide in tetrahydrofuran is added dropwise to a solution, cooled to −20° C., of 0,1 mol of methyl 5-methoxy-1H-indolecarboxylate in tetrahydrofuran. The medium is stirred for 30 minutes at this temperature, followed by dropwise addition of a solution of 0.1 mol of methyl iodide in tetrahydrofuran. Once the addition is complete, the medium is warmed slowly to room temperature, stirred for 1 h at this temperature and filtered. The expected product is obtained after concentration of the solvent.
Melting point: 200° C.

Stage B: (5-Methoxy-1-methyl-1H-indole-2-yl)methanol

The expected product is obtained from the compound prepared in the above step according to the process described in stage B of preparation H.
Melting point: 158° C.

Stage C: 5-Methoxy-1-methyl-1H-indole-2-carboxaldehyde

The expected product is obtained from the compound preprared in the above step according to the process described in stage B of preparation L.
Melting point: 88–90° C.

Stage D: 5-Methoxy-1-methyl-2-vinyl-1H-indole

The expected product is obtained from the compound prepared in the above step according to the process described in stage A of preparation I.
Melting point: 87–89° C.

Stage E: Dimethyl 6-methoxy-9-methyl-2,9-dihydro-1H-carbazole-3,4-dicarboxylate

The product is obtained from the compound prepared in the above step according to the process described in stage E of preparation H.
Melting point: 245° C.

Stage F: Dimethyl 6-methoxy-9-methyl-1H-carbazole-3,4-dicarboxylate

The product is obtained from the compound prepared according to the process described in stage E of preparation A.
Melting point: 211° C.

Stage G: 6-Methoxy-9-methyl-1H-carbazole-3,4-dicarboxylic acid

The product is obtained from the above compound according to the process described in stage F of preparation A.

Stage H: 9-Methoxy-6-methyl-6H-2-oxa-6-azacyclopenta[c]fluorene- 1,3-dione

The product is obtained from the above compound according to the process described in stage G of preparation A.

PREPARATION P
5,6-Dimethyl-6H-2-oxa-6-azacyclopenta[c]fluorene-1,3-dione
Stage A: 2-Isopropenyl-1-methyl-1H-indole The expected product is obtained from N-methyl-1H-indole according to the method described in *J.O.C.*, 59, (15), 4250, 1994.

Stage B: Dimethyl 1,9-dimethyl- 1,2-dihydro-9H-carbazole-3,4-dicarboxylate

The expected product is obtained from the product of stage A according to the process described in stage E of preparation H.

Stage C: Dimethyl 1,9-dimethyl-9H-carbazole-3,4-dicarboxylate.

The expected product is obtained from the above product according to the process described in stage E of preparation A.

Stage D: 1,9-Dimethyl-9H-carbazole-3,4-dicarboxylic acid

The expected product is obtained from the above compound according to the process described in stage F of preparation A.

Stage E: 5,6-Dimethyl-6H-2-oxa-6-azacyclopenta[c]fluorene-1,3-dione

The expected product is obtained from the above compound according to the process described in stage G of preparation A.

PREPARATION Q

N,N'-Bis[2-(1(R)-methylaminoethyl)ethane]-1,2-diamine

The expected product is obtained from N-(tert-butoxycarbonyl)-D-alanine and ethylenediamine according to the method described in *J. Med. Chem*, 40, 449, 1997.

EXAMPLE 1

N,N'-Bis[2-(2-aza-1,3-dioxo-10-methoxy-cyclopenta[c]phenanthren-2-yl)ethyl]ethane-1,2-diamine bismethanesulfonate A solution of 40 mmol of N-1-[2-(2-aminoethylamino)ethyl]ethane-1,2-diamine in 20 ml of tolune is added dropwise to 80 imol of the compound described in preparation A in 1 l of toluene, stirred at 80° C. The reaction mixture is then maintained at reflux for 17 h, filtered while hot and then concentrated under vacuum. The residue, taken up in 300 ml of ethanol, is stirred at reflux for 3 h and then filtered while hot. After cooling to room temperature, the crude product is isolated by filtration and then purified by chromatography on silica. The product in base form thus collected is stirred in 450 ml of dichloromethane. A solution of two equivalents of methanesulphonic acid in dichloromethane is added to this medium and stirring is continued for 5 hours. The product is then filtered, washed with ether and dried.

EXAMPLE 2

N,N'-Bis[2-(2-aza-1,3-dioxo-10-methoxy-cyclopenta[c]phenanthren-2-yl)ethyl]propane-1,3-diamine bismethanesulfonate The expected product is obtained according to the process described in Example 1, starting with the compound described in preparation A and N-1-[3-(2-aminoethylamino)propyl]ethane-1,2-diamine.

EXAMPLE 3

1,8-Bis(2-aza-1,3-dioxo-10-methoxycyclopenta[c]phenanthren-2-yl)-4-azaoctane methanesulfonate The expected product is obtained according to the process described in Example 1, starting with the compound described in preparation A and 4-azaoctane-1,8-diamine. Melting point: 294° C.

EXAMPLE 4

N,N-Bis[3-(2-aza-1,3-dioxo-10-methoxycyclopenta[c]-phenanthren-2-yl)propyl]methylamine methanesulfonate The expected product is obtained according to the process described in Example 1, starting with the compound described in preparation A and N,N-bis(3-aminopropyl)methylamine.

EXAMPLE 5

N,N'-Bis[2-(2-aza-1,3-dioxocyclopenta[c]phenanthren-2-yl)ethyl]-propane-1,3-diamine bismethanesulfonate The expected product is obtained according to the process described in Example 1, starting with the compound described in preparation B and N-1-[3-(2-aminoethylamino)propyl]ethane-1,2-diamine.

| | Elemental microanalysis | | | |
| --- | --- | --- | --- | --- |
| | C % | H % | N % | S % |
| Calculated | 60.58 | 4.96 | 6.89 | 7.89 |
| Found | 60.79 | 4.91 | 6.83 | 7.79 |

EXAMPLE 6

N,N'-Bis[2-(2-aza-1,3-dioxocyclopenta[c]phenanthren-2-yl)ethyl]ethane-1,2-diamine bismethanesulfonate The expected product is obtained according to the process described in Example 1, replacing the product described in preparation A by the product described in preparation B.

| | Elemental microanalysis | | | |
| --- | --- | --- | --- | --- |
| | C % | H % | N % | S % |
| Calculated | 60.14 | 4.79 | 7.01 | 8.03 |
| Found | 60.32 | 4.89 | 6.97 | 8.02 |

EXAMPLE 7

N,N'-Bis[2-(2-aza-1,3-dioxonaphtho[2,3-c]furan-2-yl)ethyl]ethane-1,2-diamine bismethanesulfonate The expected product is obtained according to the process described in Example 1, replacing the product described in preparation A by the product described in preparation C.

| | Elemental microanalysis | | | |
| --- | --- | --- | --- | --- |
| | C % | H % | N % | S % |
| Calculated | 55.01 | 4.90 | 8.02 | 9.18 |
| Found | 54.40 | 4.97 | 7.77 | 8.32 |

EXAMPLE 8

N,N'-Bis[2-(2-aza-1,3-dioxo-8-thiadicyclopenta[a,h]naphthalen-2-yl)ethyl]ethane-1,2-diamine bismethanesulfonate The expected product is obtained according to the process described in Example 1, replacing the product described in preparation A by the product described in preparation D.

| | Elemental microanalysis | | | |
|---|---|---|---|---|
| | C % | H % | N % | S % |
| Calculated | 45.50 | 4.22 | 5.59 | 19.18 |
| Found | 45.96 | 4.11 | 5.63 | 19.88 |

EXAMPLE 9

N,N-Bis[3-(2-aza-1,3-dioxo-8-thiadicyclopenta[a,h] naphthalen-2-yl)-propyl]methylamine methanesulfonate The expected product is obtained according to the process described in Example 1, starting with the compound described in preparation D and N,N-bis(3-aminopropyl) methylamine.

EXAMPLE 10

N,N'-Bis[2-(2,9-diaza-9,10-dimethyl-1,3-dioxo-6-methoxy-9H- cyclopenta[b]fluoren-2-yl)ethyl] ethane-1,2-diamine bismethane-sulfonate The expected product is obtained according to the process described in Example 1, replacing the product described in preparation A by the product described in preparation E and working in ethanol instead of toluene.

| | Elemental microanalysis | | | |
|---|---|---|---|---|
| | C % | H % | N % | S % |
| Calculated | 56.71 | 5.42 | 9.41 | 7.18 |
| Found | 56.71 | 5.61 | 9.51 | 7.11 |

EXAMPLE 11

N,N'-Bis[2-(2,9-diaza-9,10-dimethyl-1,3-dioxo-6-methoxy-9H-cyclopenta[b]fluoren-2-yl)ethyl] propane-1,3-diamine bismethanesulfonate The expected product is obtained according to the process described in Example 1, starting with the compound described in preparation E and N-1-[3-(2-aminoethylamino) propyl]ethane-1,2-diamine and working in ethanol instead of toluene.

| | Elemental microanalysis | | | |
|---|---|---|---|---|
| | C % | H % | N % | S % |
| Calculated | 56.94 | 5.56 | 9.27 | 7.02 |
| Found | 57.49 | 5.61 | 9.35 | 7.13 |

EXAMPLE 12

N,N-Bis[3-(2,9-diaza-9,10-dimethyl-1,3-dioxo-6-methoxy-9H-cyclo-penta[b]fluoren-2-yl)propyl] methylamine methanesulfonate The expected product is obtained according to the process described in Example 1, starting with the compound described in preparation E and N,N-bis(3-aminopropyl) methylamine and working in ethanol instead of toluene.

| | Elemental microanalysis | | | |
|---|---|---|---|---|
| | C % | H % | N % | S % |
| Calculated | 63.38 | 5.70 | 8.80 | 4.03 |
| Found | 64.19 | 5.82 | 9.18 | 4.03 |

EXAMPLE 13

1,8-Bis(2,9-diaza-9,10-dimethyl-1,3-dioxo-6-methoxy-9H-cyclopenta[b]fluoren-2-yl)-4-azaoctane methanesulfonate The expected product is obtained according to the process described in Example 1, starting with the compound described in preparation E and 4-azaoctane-1,8-diamine and working in ethanol instead of toluene.

| | Elemental microanalysis | | | |
|---|---|---|---|---|
| | C % | H % | N % | S % |
| Calculated | 63.38 | 5.70 | 8.80 | 4.03 |
| Found | 62.95 | 5.80 | 8.96 | 4.02 |

EXAMPLE 14

N,N-Bis[3-(2,9-diaza-9,10-dimethyl-1,3-dioxo-6-methoxy-9H-cyclopenta[b]fluoren-2-yl)propyl] amine methanesulfonate The expected product is obtained according to the process described in Example 1, starting with the compound described in preparation E and N,N-bis(3-aminopropyl) amine and working in ethanol instead of toluene.

| | Elemental microanalysis | | | |
|---|---|---|---|---|
| | C % | H % | N % | S % |
| Calculated | 62.98 | 5.54 | 8.96 | 4.10 |
| Found | 62.91 | 5.63 | 8.78 | 4.17 |

EXAMPLE 15

N,N'-Bis[3-(2,9-diaza-9,10-dimethyl-1,3-dioxo-6-methoxy-9H-cyclo-penta[b]fluoren-2-yl)propyl] ethane-1,2-diamine bismethanesulfonate The expected product is obtained according to the process described in Example 1, starting with the product described in preparation E and N-[2-(3-aminopropylamino)ethyl] propane-1,3-diaamine, working in ethanol instead of toluene.

| | Elemental microanalysis | | | |
|---|---|---|---|---|
| | C % | H % | N % | S % |
| Calculated | 57.38 | 5.69 | 9.12 | 6.96 |
| Found | 57.08 | 5.66 | 8.64 | 6.50 |

EXAMPLE 16

N,N'-Bis[2-(2-aza-1,3-dioxo-10-hydroxycyclopenta [c]phenanthren-2-yl)ethyl]ethane-1,2-diamine hydrobromide A suspension of 1 mmol of the compound of Example 1 in 40 ml of 47% hydrobromic acid is maintained at reflux for 8 hours. After cooling to room temperature, the solid is filtered off, washed with water and taken up in refluxing ethanol for 1 h. After filtration, the expected product is obtained.

EXAMPLE 17

N,N-Bis[3-(2-aza-1,3-dioxo-10-hydroxycyclopenta[c]phenanthren-2-yl)propyl]methylamine hydrobromide The expected product is obtained according to the process described in Example 16, starting with the compound of Example 4.

EXAMPLE 18

N,N'-Bis[2-(2,9-diaza-9,10-dimethyl-1,3-dioxo-6-hydroxy-9H-cyclopenta[b]fluoren-2-yl)ethyl]ethane-1,2-diamine dihydrobromide The expected product is obtained according to the process described in Example 16, starting with the compound of Example 10.

EXAMPLE 19

N,N'-Bis[2-(2,9-diaza-9,10-dimethyl-1,3-dioxo-6-hydroxy-9H-cyclopenta[b]fluoren-2-yl)ethyl]propane-1,3-diamine dihydrobromide The expected product is obtained according to the process described in Example 16, starting with the compound of Example 11.

| Elemental microanalysis | | | | |
|---|---|---|---|---|
| | C % | H % | N % | Br % |
| Calculated | 55.20 | 4.75 | 9.90 | 18.83 |
| Found | 55.11 | 4.44 | 9.73 | 17.53 |

EXAMPLE 20

1,8-Bis(2,9-diaza-9,10-dimethyl-1,3-dioxo-6-hydroxy-9H-cyclopenta[b]fluoren-2-yl)-4-azaoctane hydrobromide The expected product is obtained according to the process described in Example 16, starting with the compound of Example 13.

| Elemental microanalysis | | | | |
|---|---|---|---|---|
| | C % | H % | N % | Br % |
| Calculated | 62.24 | 5.09 | 9.30 | 10.62 |
| Found | 63.04 | 5.02 | 9.25 | 9.57 |

EXAMPLE 21

N,N'-Bis[3-(2,9-diaza-9,10-dimethyl-1,3-dioxo-6-hydroxy-9H-cyclo-penta[b]fluoren-2-yl)propyl]ethane-1,2-diamine The expected product is obtained according to the process described in Example 16, starting with the compound of Example 15.

| Elemental microanalysis | | | | |
|---|---|---|---|---|
| | C % | H % | N % | Br % |
| Calculated | 55.70 | 4.91 | 9.74 | 18.53 |
| Found | 55.88 | 4.68 | 9.13 | 17.87 |

EXAMPLE 22

1-[2-(1,3-Dioxo-2,3-dihydro-5-nitrobenzo[d,e]isoquinolin-2-yl)ethyl]-3-[2-(2-aza-1,3-dioxo-10-methoxycyclopenta[c]phenanthren-2-yl)ethyl]propane-1,3-diamine bismethanesulfonate Stage A: 2-[2-(3-Aminopropylamino)ethylamino]-5-nitrobenzo[d,e]isoquinoline-1,3-dione trimethanesulfonate A solution, at 0° C., of 50 mmol of 3-nitronaphthoic anhydride in 300 ml of THF is added dropwise to a stirred solution at 0° C. of 50 mmol of N,N'-bis(2-aminoethyl)propane-1,3-diamine in 200 ml of THF. Once the addition is complete, the reaction mixture is stirred for 3 hours at room temperature, for 2 hours at reflux and is then filtered while hot. The filtrate is stirred at room temperature and 150 mmol of methanesulfonic acid in 100 ml of THF are added dropwise. The precipitate is filtered off, taken up in 1 l of ethanol and maintained at reflux for 2 hours. The insoluble material is filtered off and the filtrate is cooled. The desired product is obtained after filtration, in a yield of 32%.

Stage B: 1-[2-(1,3-Dioxo-2,3-dihydro-5-nitrobenzo[d,e]isoquinolin-2-yl)ethyl]-3-[2-(2-aza-1,3-dioxo-10-methoxycyclopenta[c]phenanthren-2-yl)ethyl]propane-1,3-diamine bismethanesulfonate 5 mmol of the compound described in preparation A are added portionwise to a solution of 5 mmol of the compound prepared in the above stage and 15 mmol of diisopropylethylamine in 1 l of ethanol stirred at room temperature. Once the addition is complete, the mixture is maintained at reflux for 15 hours and then filtered while hot. The cooled filtrate is filtered and the solid is purified by chromatography on silica with the eluent 95 CH$_2$Cl$_2$/5 MeOH/0.1 NH$_2$OH. The fractions containing the product are combined and concentrated, the residue is taken up in 1 l of methylene chloride and 2 equivalents of methanesulfonic acid are added. The product is isolated by filtration.

EXAMPLE 23

1-[2-(1,3-Dioxo-2,3-dihydro-5-nitrobenzo[d,e]isoquinolin-2-yl)ethyl]-2-[2-(2-aza-1,3-dioxo-10-methoxycyclopenta[c]phenanthren-2-yl)ethyl]ethane-1,2-diamine bismethanesulfonate The expected product is obtained according to the process described in Example 22, using N,N'-bis(2-aminoethyl)ethane-1,2-diamine in stage A.

| Elemental microanalysis | | | | |
|---|---|---|---|---|
| | C % | H % | N % | S % |
| Calculated | 53.00 | 4.52 | 8.31 | 8.37 |
| Found | 53.00 | 4.64 | 8.40 | 8.54 |

EXAMPLE 24

N,N'-Bis[2-(2-aza-6-oxacyclopenta[c]fluorene-1,3-dion-2-yl)ethyl]propane-1,3-diamine bismethanesulfonate The expected product is obtained according to the process described in Example 1, starting with the compound described in preparation I and N-1-[3-(2-aminoethylamino)propyl]ethane-1,2-diamine.

| | Elemental microanalysis | | | |
|---|---|---|---|---|
| | C % | H % | N % | S % |
| Calculated | 56.05 | 4.58 | 7.07 | 8.09 |
| Found | 56.15 | 4.48 | 7.02 | 8.30 |

EXAMPLE 25

N,N'-Bis[2-(2-aza-1,3-dioxo-10-nitrocyclopenta[c]phenanthren-2-yl)ethyl]propane-1,3-diamine bismethanesulfonate The expected product is obtained according to the process described in Example 1, starting with the compound described in preparation F and N-1-[3-(2-aminoethylamino)propyl]ethane-1,2-diamine.

| | Elemental microanalysis | | | |
|---|---|---|---|---|
| | C % | H % | N % | S % |
| Calculated | 54.54 | 4.24 | 9.31 | 7.10 |
| Found | 54.73 | 4.27 | 9.24 | 7.24 |

EXAMPLE 26

N,N'-Bis[2-(2-aza-10-oxa-1,3-dioxocyclopenta[a]fluoren-2-yl)ethyl]propane-1,3-diamine bismethanesulfonate The expected product is obtained according to the process described in Example 1, starting with the compound described in preparation H and N-1-[3-(2-aminoethylamino)-propyl]ethane-1,2-diamine.

| | Elemental microanalysis | | | |
|---|---|---|---|---|
| | C % | H % | N % | S % |
| Calculated | 56.05 | 4.58 | 7.07 | 8.09 |
| Found | 56.48 | 4.66 | 7.03 | 7.85 |

EXAMPLE 27

N,N'-Bis[2-(2-aza-1,3-dioxo-10-methoxycyclopenta[c]phenanthren-2-yl)(1(R)-methyl)ethyl)ethane-1,2-diamine bismethanesulfonate The expected product is obtained according to the process described in Example 1, starting with the compound described in preparation A and the compound described in preparation Q.

| | Elemental microanalysis | | | |
|---|---|---|---|---|
| | C % | H % | N % | S % |
| Calculated | 59.58 | 5.23 | 6.32 | 7.23 |
| Found | 59.77 | 5.26 | 6.15 | 6.99 |

EXAMPLE 28

N,N'-Bis[2-(2-aza-1,3-dioxocyclopenta[b]phenanthren-2-yl)ethyl]propane-1,3-diamine bismethanesulfonate The expected product is obtained according to the process described in Example 1, starting with the compound described in preparation G and N-1-[3-(2-aminoethylamino)propyl]ethane-1,2-diamine.

EXAMPLE 29

N,N'-Bis[2-(2-aza-1,3-dioxo-10-methyl-10H-pyrrolo[3,4-a]carbazol-2-yl)ethyl]propane-1,3-diamine bismethanesulfonate The expected product is obtained according to the process described in Example 1, starting with the compound described in preparation K and N-1-[3-(2-aminoethylamino)propyl]ethane-1,2-diamine.

| | Elemental microanalysis | | | |
|---|---|---|---|---|
| | C % | H % | N % | S % |
| Calculated | 57.20 | 5.17 | 10.26 | 7.83 |
| Found | 57.18 | 5.09 | 9.92 | 8.04 |

EXAMPLE 30

N,N'-Bis[2-(2-aza-1,3-dioxo-6-thiacyclopenta[c]fluoren-2-yl)ethyl]propane-1,3-diamine bismethanesulfonate The expected product is obtained according to the process described in Example 1, starting with the compound described in preparation J and N-1-[3-(2-aminoethylamino)propyl]ethane-1,2-diamine.

| | Elemental microanalysis | | | |
|---|---|---|---|---|
| | C % | H % | N % | S % |
| Calculated | 53.87 | 4.40 | 6.79 | 15.55 |
| Found | 53.26 | 4.81 | 6.88 | 15.88 |

EXAMPLE 31

N,N'-Bis[2-(2-aza-1,3-dioxo-6-methyl-6H-pyrrolo[3,4-c]carbazol-2-yl)ethyl]propane-1,3-diamine bismethanesulfonate The expected product is obtained according to the process described in Example 1, starting with the compound described in preparation L and N-1-[3-(2-aminoethylamino)propyl]ethane-1,2-diamine.

| | Elemental microanalysis | | | |
|---|---|---|---|---|
| | C % | H % | N % | S % |
| Calculated | 57.20 | 5.17 | 10.26 | 7.83 |
| Found | 57.18 | 5.09 | 9.92 | 8.04 |

EXAMPLE 32

N,N'-Bis[2-(2-aza-1,3-dioxo-10-methoxycyclopenta[c]phenanthren-2-yl)ethyl]butane-1,4-diamine bismethanesulfonate The expected product is obtained according to the process described in Example 1, starting with the compound described in preparation A and N-1-[4-(2-aminoethylamino)butyl]ethane-1,2-diamine.

| | Elemental microanalysis | | | |
|---|---|---|---|---|
| | C % | H % | N % | S % |
| Calculated | 59.58 | 5.23 | 6.32 | 7.23 |
| Found | 59.17 | 5.37 | 6.26 | 6.98 |

EXAMPLE 33

N,N'-Bis[2-(2-aza-1,3-dioxo-6H-pyrrolo[3,4-c]carbazol-2-yl)ethyl]propane-1,3-diamine bismethanesulfonate The expected product is obtained according to the process described in Example 1, starting with the compound described in preparation M and N-1-[3-(2-aminoethylamino)propyl]ethane-1,2-diamine.

| | Elemental microanalysis | | | |
|---|---|---|---|---|
| | C % | H % | N % | S % |
| Calculated | 56.19 | 4.84 | 10.63 | 8.11 |
| Found | 56.34 | 5.08 | 10.71 | 8.24 |

EXAMPLE 34

1-[2-(1,3-Dioxo-2,3-dihydro-5-nitrobenzo[d,e]isoquinolin-2-yl)ethyl]-3-[2-(2-aza-1,3-dioxo-6-methyl-6H-pyrrolo[3,4-c]carbazol-2-yl)ethyl]propane-1,3-diamine bismethanesulfonate The expected product is obtained according to the process described in Example 22, using in stage B the compound described in preparation L.

| | Elemental microanalysis | | | |
|---|---|---|---|---|
| | C % | H % | N % | S % |
| Calculated | 53.33 | 4.72 | 10.36 | 7.91 |
| Found | 53.80 | 4.70 | 10.46 | 7.88 |

EXAMPLE 35

N,N'-Bis[2-(2-aza-1,3-dioxo-6-methyl-9-methoxy-6H-pyrrolo-[3,4-c]-carbazol)-2-yl]propane-1,3-diamine bismethanesulfonate The expected product is obtained according to the process described in Example 1, using the compound described in preparation O and N-1-[3-(2-aminoethylamino)propyl]ethane-1,2-diamine.

EXAMPLE 36

N,N'-Bis[2-(2-aza-1,3-dioxo-6-methyl-6H-pyrrolo[3,4-c]carbazol-2-yl)(1-(R)-methyl)ethyl]ethane-1,2-diamine bismethanesulfonate The expected product is obtained according to the process described in Example 1, using the compound described in preparation L and that described in preparation Q.

EXAMPLE 37

1-[2-(1,3-Dioxo-2,3-dihydro-5-nitrobenzo[d,e]isoquinolin-2-yl)(1-(R)-methyl)ethyl]-2-[2-(2-aza-1,3-dioxo-6-methyl-6H-pyrrolo[3,4-c]carbazol-2-yl)(1-(R)-methyl)ethyl]ethane-1,2-diamine bismethanesulfonate The expected product is obtained according to the process described in Example 22, using in stage B the compound described in preparation L.

EXAMPLE 38

N,N'-Bis[2-(2-aza-1,3-dioxo-6-methyl-6H-9-nitropyrrolo[3,4-c]carbazol-2-yl)(1-(R)-methyl)ethyl]ethane-1,2-diamine bismethanesulfonate The expected product is obtained according to the process described in Example 1, using the compound described in preparation N.

EXAMPLE 39

N,N'-Bis[2-(2-aza-5,6-dimethyl-1,3-dioxo-6H-pyrrolo[3,4,-c]carbazol-2-yl)(1-(R)-methyl)ethyl]ethane-1,2-diamine bismethanesulfonate The expected product is obtained according to the process described in Example 1, using the compound described in preparation P.

EXAMPLE 40

1-[2-(2-Aza-1,3-dioxo-6-methyl-6H-pyrrolo[3,4-c)carbazol-2-yl)(1-(R)-methyl)ethyl]-2-[2-(2-aza-1,3-dioxo-10-methoxycyclopenta[c]phenanthren-2-yl)(1-(R)-methyl)ethyl]ethane-1,2-diamine bismethanesulfonate The expected product is obtained according to the process described in Example 22, using in stage A the compound described in preparation A and in stage B the compound described in preparation L.

PHARMACOLOGICAL STUDY OF THE COMPOUNDS OF THE INVENTION

EXAMPLE 41

In Vitro Proliferation

This test makes it possible to measure the anti-proliferative power of a compound in vitro by determining the concentration of product which inhibits cell growth by 50% when compared with untreated control cells ($IC_{50}$).

This is a colorimetric test based on cleavage, by reduction with the mitochondrial succinate dehydrogenase of live cells, of a soluble tetrazolium salt, 3-(4,5-dimethylthiazol-2-yl)-2,5-diphenyltetrazolium bromide, or MTT, into purple formazan crystals which are insoluble in the culture medium.

In order to ensure that they adhere fully, the cells are inoculated at a density of 625 cells per well in 96-well plates, 24 hours before being incubated at 37° C., continuously and in the presence of a range of concentrations of the test product. After four periods of doubling of the cell population (determined after studying the line growth kinetics), the live cells are stained with MTT (1/10th of the volume of medium is added to the wells, solution containing 5 mg/ml in PBS) for 4 hours at 37° C. At the end of this incubation, a volume equal to that of the well of a solution of SDS is added (20% SDS, 50% dimethylforimamide in water, pH 4.7) which, after exposure overnight, dissolves the formazan crystals. The optical density of the medium is then measured at 540 nm by a Titertek multiscan MCC plate reader (Labsystem). Calibration curves were produced for each of the lines from cells inoculated at increasing densities, and made it possible to establish a linear relationship between the number of live cells and the optical density read.

The lines used in this test are:
the line LLC: Lewis lung carcinoma of murine origin,
the line HT-29: colon carcinoma of human origin.

The results obtained on these two lines show that the compounds of the invention have very strong anti-proliferative power.

By way of example, the $IC_{50}$ of the compound of Example 22 is equal to 53.60 nM on the LLC line and equal to 1.4 nM on the HT-29 line.

EXAMPLE 42

In Vivo Antitumor Activity

The antitumor activity of the compounds of the invention was studied in Nude mice. Fragments of human epidermoid carcinoma KB-3-1 were grafted subcutaneously onto 4- to 6-week-old Nude Swiss female mice weighing from 20 to 22 g. When the tumors reach a diameter of about 6 mm, the mice are divided among the control group and the treated group (7 mice per group) so as to obtain an identical average tumor volume in each of the groups. The test product is administered via the i.v. route; 1 injection per day for 5 days. The tumors are measured twice a week and the tumor volume is calculated according to the formula: volume= (length×width²)/2. The antitumor activity is evaluated by virtue of 2 parameters: the average T/C, expressed as a percentage, and the SGD (specific growth delay).

Average T/C (%) at a time t=100×(Vt/V0) average treated/ (Vt/V0) average control with Tt:tumor volume at time t; V0: tumor volume at the start of the treatment.

SGD=(Td treated−Td control)/Td control with Td=average doubling time of the tumor. The results obtained with the products of the invention show that they strongly inhibit tumor growth.

By way of example, the compound of Example 1, administered at a dose of 15 mg/kg via the i.v. route for 5 days, gives the following results: 14 days after the start of the treatment, the average T/C is 26% (thus 74% inhibition) and the SGD is 1.3. Furthermore, the treatment does not cause any weight loss and it is thus well tolerated.

EXAMPLE 43

Pharmaceutical Composition

Preparation formula for 1000 tablets containing 10 mg doses

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

What is claimed is:

1. A compound selected from those of formula (I):

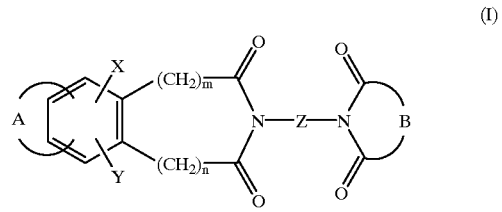

in which:

m and n, which may be identical or different, represent 0,

X and Y, which may be identical or different, represent hydrogen or halogen or linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylamino, or dialkylamino, Z represents a linear or branched $C_4$ to $C_{12}$ alkylene chain in which one or more —$CH_2$— groups are optionally replaced by any one of the following atoms or groups: —NR— (in which R represents hydrogen or linear or branched ($C_1$–$C_6$) alkyl), —O—, —S—, —SO—, —$SO_2$—, or —CONH—, or by a substituted or unsubstituted heterocylcic group, A forms, with two adjacent carbon atoms of the phenyl ring:
a substituted or unsubstituted heterocycle,

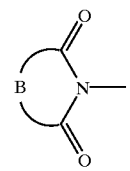

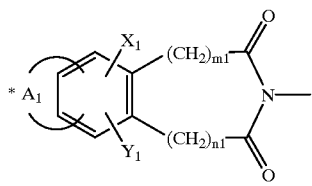

(I)

in which:

$m_1$ and $n_1$, which may be identical or different, represent 0

$X_1$ and $Y_1$, which may be identical or different, represent hydrogen or halogen or linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylarino, or dialkylamino, $A_1$ forms, with two adjacent carbon atoms of the phenyl ring:

a substituted or unsubstituted heterocycle, its isomers and their addition salts with a pharmaceutically-acceptable acid or base.

2. The compound of claim 1, wherein A represents, with two adjacent carbon atoms of the phenyl ring, a substituted or unsubstituted heterocycle chosen from optionally substituted indole, optionally substituted benzothiophene, and optionally substituted benzofuran rings.

3. A compound of claim 1, wherein Z represents a $C_4$ to $C_{12}$ alkylene chain in which 1, 2 or 3 —$CH_2$— groups are replaced by 1, 2 or 3 —NR-groups in which R represents hydrogen or linear or branched ($C_1$–$C_6$) alkyl.

4. The compound of claim 1, wherein

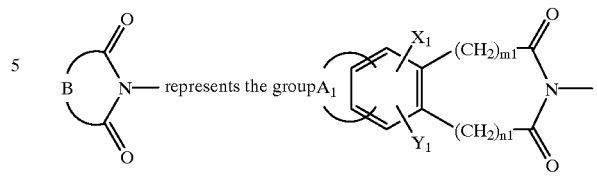

in which:

$m_1$ and $n_1$, which may be identical or different, represent 0

$X_1$ and $Y_1$, which may be identical or different, represent hydrogen or halogen or linear or branched ($C_1$–$C_6$) alkyl, linear or branched ($C_1$–$C_6$) trihaloalkyl, linear or branched ($C_1$–$C_6$) alkoxy, hydroxyl, cyano, nitro, amino, alkylamino, or dialkylamino, $A_1$ forms, with two adjacent carbon atoms of the phenyl ring:

a substituted or unsubstituted heterocycle, its optical isomers and its addition salts with a pharmaceutically-acceptable acid or base.

5. A method for treating a living body afflicted with a cancer comprising the step of administering to the living body an amount of a compound of claim 1 which is effective for amelioration thereof.

6. A pharmaceutical composition useful in the treatment of cancer method comprising as active principle an effective anti-cancer amount of a compound as claimed in claim 1, together with one or more pharmaceutically-acceptable excipients or vehicles.

7. A compound of claim 1 selected from N,N'-Bis[2-(2-aza-5,6-dimethyl-1,3-dioxo-6H-pyrrolo{3,4-c]carbazol-2-yl)(1-(R)-methyl)ethyl]ethane-1,2-diamine and its bis-methanesulfonate.

* * * * *

UNITED STATES PATENT AND TRADEMARK OFFICE
CERTIFICATE OF CORRECTION

PATENT NO. : 6,162,822
DATED : Dec. 19, 2000
INVENTOR(S) : G. Lavielle, P. Hautefaye, G. Atassi, A. Pierre, L. Kraus-Berthier, S. Leonce

It is certified that error appears in the above-identified patent and that said Letters Patent is hereby corrected as shown below:

Title Page, [57] ABSTRACT, 5th line (below formula(I)): "alky," should read:
-- alkyl, --. ABSTRACT, page 7

Title Page, [57] ABSTRACT, 12th line (below formula(I)): "heterocylcic," should read
-- heterocyclic --. Preliminary Amendment dtd 12/24/98, IN THE ABSTRACT OF THE DISCLOSURE, line 11.

Title Page, [57] ABSTRACT, same line as the second formula: INSERT -- represents any one of the groups as defined in the description, --. ABSTRACT, line 14

Title Page, [57] ABSTRACT, At the beginning of the line under second formula: INSERT -- its optical isomers and its addition salts with a pharmaceutically-acceptable acid or base, --. ABSTRACT, line 14

Title Page, [57] ABSTRACT, last two lines: Insert -- which -- before "are" and change "agent" to -- agents --. Preliminary Amendment dtd 12/24/98, IN THE ABSTRACT OF THE DISCLOSURE: line 16 (last line).

Column 13, line 28: "80 imol" should read:
-- 80 mmol --. Page 22, line 16.

Column 16, line 51: "1,3-diaamine," should read:
-- 1,3-diamine, --. Page 26, line 22

UNITED STATES PATENT AND TRADEMARK OFFICE
CERTIFICATE OF CORRECTION

PATENT NO. : 6,162,822
DATED : Dec. 19, 2000
INVENTOR(S) : G. Lavielle, P. Hautefaye, G. Atassi, A. Pierre, L. Kraus-Berthier, S. Leonce Page 2 of 3

It is certified that error appears in the above-identified patent and that said Letters Patent is hereby corrected as shown below:

Column 23, line 30: "dimethylforimamide" should read: -- dimethylformamide --.
Page 34, line 24

Column 24, lines 54-55: "heterocylcic group," should read: -- heterocyclic group, --.
Preliminary Amendment dtd 12/24/98, Claim 1, line 11.

Column 24, first line under second formula: INSERT -- represents any one of the following groups --. Page 37, last line on page.

Column 25, line 18: "alkylarino," should read: -- alkylamino --. Page 38, line 7

Column 25, line 24: At the beginning of the line, after "its" INSERT -- optical --; and replace "their" with the word -- its --. Page 2 of Preliminary Amendment dtd 12/24/98, Claim 1 on page 38, line 20.

Column 25, line 26: At the beginning of the line, change the word "The" to -- A --. Page two of Preliminary Amendment dtd 12/24/98, Claim 3, line 1.

UNITED STATES PATENT AND TRADEMARK OFFICE
CERTIFICATE OF CORRECTION

PATENT NO. : 6,162,822
DATED : Dec. 19, 2000
INVENTOR(S) : G. Lavielle, P. Hautefaye, G. Atassi, A. Pierre, L. Kraus-Berthier, S. Leonce It is certified that error appears in the above-identified patent and that said Letters Patent is hereby corrected as shown below:

Column 25, line 30: "benzothiophene," should read: -- benzo[b]thiophene --. Page 39, line 4

Column 25, line 31: "benzofuran rings." should read: -- benzo[b]furan rings --. Page 39, line 5

Column 26, line 27: Delete the word "method". Page 2 of Preliminary Amendment dtd 12/24/98, Claim 13, line 1.

Signed and Sealed this

Twenty-ninth Day of May, 2001

NICHOLAS P. GODICI

Attest:

Attesting Officer

Acting Director of the United States Patent and Trademark Office